(12) United States Patent
Uhland et al.

(10) Patent No.: US 6,827,250 B2
(45) Date of Patent: Dec. 7, 2004

(54) METHODS FOR HERMETICALLY SEALING MICROCHIP RESERVOIR DEVICES

(75) Inventors: Scott A. Uhland, Roslindale, MA (US); Benjamin F. Polito, Cambridge, MA (US); Stephen J. Herman, Andover, MA (US); John T. Santini, Jr., North Chelmsford, MA (US); John M. Maloney, Cambridge, MA (US)

(73) Assignee: MicroCHIPS, Inc., Bedford, MA (US)

( * ) Notice: Subject to any disclaimer, the term of this patent is extended or adjusted under 35 U.S.C. 154(b) by 0 days.

(21) Appl. No.: 10/184,259

(22) Filed: Jun. 28, 2002

(65) Prior Publication Data

US 2003/0010808 A1 Jan. 16, 2003

Related U.S. Application Data

(60) Provisional application No. 60/301,686, filed on Jun. 28, 2001.

(51) Int. Cl.[7] .............................. B23K 1/06; B23K 26/00
(52) U.S. Cl. ................................ 228/110.1; 228/124.6; 219/121.64
(58) Field of Search ................................ 228/110.1, 1.1, 228/124.6, 254; 219/121.63, 121.64

(56) References Cited

U.S. PATENT DOCUMENTS

| | | |
|---|---|---|
| 4,146,029 A | 3/1979 | Ellinwood, Jr. |
| 4,345,981 A | 8/1982 | Bennett et al. |
| 4,360,019 A | 11/1982 | Portner et al. |
| 4,507,115 A | 3/1985 | Kambara et al. |
| 4,585,652 A | 4/1986 | Miller et al. |
| 4,731,051 A | 3/1988 | Fischell |
| 4,793,825 A | 12/1988 | Benjamin et al. |
| 5,041,107 A | 8/1991 | Heil, Jr. |
| 5,167,625 A | 12/1992 | Jacobsen et al. |
| 5,170,801 A | 12/1992 | Casper et al. |

(List continued on next page.)

FOREIGN PATENT DOCUMENTS

| | | |
|---|---|---|
| DE | 197 16 683 | 6/1998 |
| WO | 01/12157 | 2/2001 |
| WO | 01/35928 | 5/2001 |
| WO | 01/41736 | 6/2001 |
| WO | 01/64344 | 9/2001 |
| WO | 01/91902 | 12/2001 |

OTHER PUBLICATIONS

Armani, et al. "Microfabrication Technology for Polycaprolactone, a Biodegradable Polymer," J. Micromech. Microeng. 10 (2000) 80–84.
Becker, et al. "Polymer Microfabrication Methods for Microfluidic Analytical Applications," Electrophoresis 2000, 21, 12–26.

(List continued on next page.)

Primary Examiner—Kiley Stoner
(74) Attorney, Agent, or Firm—Sutherland Asbill & Brennan LLP

(57) ABSTRACT

Methods are provided for hermetically sealing the reservoirs of microchip devices and for hermetically sealing the substrate assemblies in a hermetic packaging structure. In one embodiment, the method comprises (1) providing a primary substrate having a front side and a back side, the substrate comprising a plurality of reservoirs positioned between the front side and the back side, each reservoir being loaded with molecules or a secondary device for controlled release or exposure, the reservoirs having at least one opening in need of sealing, the primary substrate including one or more hermetic sealing materials; (2) providing a hermetic sealing substrate having a surface composed of one or more hermetic sealing materials; (3) positioning the hermetic sealing substrate over the reservoir openings and contacting said hermetic sealing materials of the primary substrate with said hermetic sealing materials of the hermetic sealing substrate; and (4) applying energy or a mechanical force to the contacted sealing materials effective to form a hermetic seal between the hermetic sealing substrate and the primary substrate to hermetically seal the reservoir openings.

41 Claims, 5 Drawing Sheets

U.S. PATENT DOCUMENTS

| | | | |
|---|---|---|---|
| 5,196,002 | A | 3/1993 | Hanover et al. |
| 5,200,051 | A | 4/1993 | Cozzette et al. |
| 5,252,294 | A | 10/1993 | Kroy et al. |
| 5,262,127 | A | 11/1993 | Wise et al. |
| 5,304,293 | A | 4/1994 | Tierney et al. |
| 5,318,557 | A | 6/1994 | Gross |
| 5,324,316 | A | 6/1994 | Schulman et al. |
| 5,366,454 | A | 11/1994 | Currie et al. |
| 5,368,588 | A | 11/1994 | Bettinger |
| 5,368,704 | A | 11/1994 | Madou et al. |
| 5,385,709 | A | 1/1995 | Wise et al. |
| 5,443,508 | A | 8/1995 | Giampapa |
| 5,574,313 | A | 11/1996 | McKleroy |
| 5,713,954 | A | 2/1998 | Rosenberg et al. |
| 5,797,898 | A | 8/1998 | Santini, Jr. et al. |
| 5,893,974 | A | 4/1999 | Keller et al. |
| 5,938,923 | A | 8/1999 | Tu et al. |
| 5,962,081 | A | 10/1999 | Öhman et al. |
| 5,972,027 | A | 10/1999 | Johnson |
| 5,989,445 | A | 11/1999 | Wise et al. |
| 6,062,461 | A | 5/2000 | Sparks et al. |
| 6,063,116 | A | 5/2000 | Kelleher |
| 6,114,658 | A | 9/2000 | Roth et al. |
| 6,123,861 | A | 9/2000 | Santini, Jr. et al. |
| 6,136,212 | A | 10/2000 | Mastrangelo et al. |
| 6,232,150 | B1 | 5/2001 | Lin et al. |
| 6,243,608 | B1 | 6/2001 | Pauly et al. |
| 6,436,853 | B2 | 8/2002 | Lin et al. |
| 6,491,666 | B1 * | 12/2002 | Santini et al. ............... 604/191 |
| 6,527,762 | B1 * | 3/2003 | Santini et al. ............ 604/890.1 |
| 6,537,256 | B2 * | 3/2003 | Santini et al. ............... 604/191 |
| 6,551,838 | B2 * | 4/2003 | Santini et al. ............... 436/174 |
| 2002/0072784 | A1 | 6/2002 | Sheppard, Jr. et al. |
| 2002/0099359 | A1 | 7/2002 | Santini, Jr. et al. |
| 2002/0119176 | A1 | 8/2002 | Greenberg et al. |
| 2002/0138067 | A1 | 9/2002 | Sheppard, Jr. et al. |
| 2002/0151776 | A1 * | 10/2002 | Shawgo et al. ............. 600/345 |
| 2002/0187260 | A1 * | 12/2002 | Sheppard et al. ........ 427/248.1 |
| 2003/0010808 | A1 * | 1/2003 | Uhland et al. ........... 228/110.1 |
| 2003/0049865 | A1 * | 3/2003 | Santini et al. ............... 436/518 |
| 2003/0100865 | A1 * | 5/2003 | Santini et al. ............... 604/161 |
| 2003/0104590 | A1 * | 6/2003 | Santini et al. ............... 435/174 |
| 2003/0152679 | A1 * | 8/2003 | Garwood .................... 426/392 |
| 2003/0178403 | A1 | 9/2003 | Lemmerhirt et al. |

OTHER PUBLICATIONS

Bremus–Kobberling, et al., "Laser Microperforation of a Retina Implant," Presentation at Microtechnology Conference, Germany, Sep. 25–26, 2000.

Cheng, et al. "Localized Silicon Fusion and Eutectic Bonding for MEMS Fabrication and Packaging," J. Microelectromechanical Systems, vol. 9, No. 1 (2000).

Low, et al., "Microactuators Towards Microvalves for Responsive Controlled Drug Delivery," *Sensors & Actuators B 67:* 149–60 (2000).

Madou & Florkey, "From Batch to Continuous Manufacturing of Microbiomedical Devices," *Chem. Rev., 100:* 2679–92 (2000).

Madou, *Fundamentals of Microfabrication,* pp. 468–512 (CRC Press 1997).

Madou & He, "Exploitation of a Novel Artificial Muscle for Controlled Drug Delivery," pp. 495–497 (1999).

Schwarz, et al., "Micro Implantable Visual Prostheses," $1^{st}$ Annual Int'l IEEE–EMBS Special Topic Conference on Microtechnologies in Medicine & Biology, Lyon, France (Oct. 12–14, 2000).

Olson, "Parylene Conformal Coating and Its Application for Electronics," Nova Tran Parylene Coating Services, Proc. Int'l Electronics Packaging Conf., vol. 1 (Sep. 27, 1992).

Surbled, et al., "Array of Shape Memory Alloy One–Shot Micro–Valves for Drug Delivery", MME '99, Gif sur Yvette, France (Sep. 27–28 1999).

Surbled, et al., "Shape Memory Alloys for Micromembranes Actuation," *SPIE. 3825*: 63–70 (1999).

Yao, et al. "Low Temperature Eutectic Bonding for In–Plane Type Micro Thermoelectric Cooler," Proc. 2001 ASME Int'l Mechanical Engineering Congress & Exposition (Nov. 11–16, 2001).

* cited by examiner

| | |
|---|---|
| ▨ | Insulator/Etch Mask Material |
| ▦ | Anode and Cathode Material(s) |
| ▤ | Insulator Overlayer |
| ▢ | Reservoir Contents (e.g. Drug Formulation) |

200 # METHODS FOR HERMETICALLY SEALING MICROCHIP RESERVOIR DEVICES

CROSS-REFERENCE TO RELATED APPLICATIONS

Priority is claimed under 35 U.S.C. §119 to U.S. provisional application Ser. No. 60/301,686, filed Jun. 28, 2001.

BACKGROUND OF THE INVENTION

This invention is generally in the field of implantable miniaturized devices that provide controlled delivery or exposure of molecules or smaller devices. More specifically, the invention relates to implantable microchip devices.

U.S. Pat. No. 5,797,898 to Santini, et al. describes active or passive microchips for the delivery, i.e. release, of molecules such as drugs. These microchip devices contain reservoirs filled with the molecules to be released. In some embodiments, the reservoir openings must be sealed after they are filled to prevent leakage from or between any of the reservoirs.

One approach for sealing small reservoirs is to use a waterproof epoxy or other material impervious to any fluids surrounding the device. It is generally important, however, to avoid contacting the reservoir contents, particularly drug molecules, with chemical adhesives. The use of a chemical adhesive sealant may necessitate additional testing to determine the presence and nature of any interactions between the chemical adhesive and each drug or other chemical to be contained in and released from the reservoirs. The use of chemical adhesives also may require long times, high temperatures, and/or exposure to ultraviolet light in order to cure completely, processes that may degrade sensitive drug or chemical molecules in the reservoirs.

It is known that such adhesives and polymers generally cannot function as true hermetic seals over extended periods of time. Hermeticity, however, would be highly advantageous for microchip reservoirs to provide a controlled environment until the reservoirs are activated (i.e. opened). In fact, hermeticity likely is essential for most long term in vivo applications of such microchip devices. It would therefore be beneficial to provide methods of hermetically sealing a microchip device, including any control electronics and power source packaged with the device.

While hermetic sealing techniques are commonly found in implantable devices, such as pacemakers and cochlear implants, new or improved hermetic sealing methods are required for hermetically bonding a microchip reservoir device to an outer enclosure/packaging structure, which serves to protect the internal device components while also allowing a portion of the microchip reservoir device to contact/interface with the environment.

It would be desirable for seals incorporated within a microchip device for in vivo applications to prevent communication of drug, body fluids, or other substances between reservoirs or from the reservoirs into other portions of the microchip device. In addition, the seal desirably should withstand mechanical forces and chemical attack over time, and should not interfere with the process of opening reservoir caps and other aspects of the release processes. The materials forming the seals desirably are biocompatible, biostable, have very low or no permeability to water vapor and other materials, and should not react with the drug or other reservoir contents. Furthermore, the process of sealing should not degrade the reservoir contents, for example due to high temperatures, excessive vibratory forces, or exposure to incompatible chemicals or materials. It therefore would be advantageous to provide devices and methods for sealing the reservoirs of microchip devices for the controlled release of drugs and other molecules, which satisfy these several sealing parameters.

SUMMARY OF THE INVENTION

Methods are provided for hermetically sealing the reservoirs of microchip devices and for hermetically sealing the substrate assemblies in a hermetic packaging structure. In one embodiment, the method comprises (1) providing a primary substrate having a front side and a back side, the substrate comprising a plurality of reservoirs positioned between the front side and the back side, each reservoir being loaded with molecules or a secondary device for controlled release or exposure, the reservoirs having at least one opening in need of sealing, the primary substrate including one or more hermetic sealing materials; (2) providing a hermetic sealing substrate having a surface composed of one or more hermetic sealing materials; (3) positioning the hermetic sealing substrate over the reservoir openings and contacting said hermetic sealing materials of the primary substrate with said hermetic sealing materials of the hermetic sealing substrate; and (4) applying energy or a mechanical force to the contacted sealing materials effective to form a hermetic seal between the hermetic sealing substrate and the primary substrate to hermetically seal the reservoir openings.

In one embodiment, the energy can be applied through a welding process, such as one that comprises ultrasonic welding or laser welding. In another embodiment, the energy can be applied by heating to cause a reaction between the hermetic sealing materials of the primary substrate and the hermetic sealing materials of the hermetic sealing substrate. Preferably, the reaction is a eutectic reaction, for example, to form a eutectic bond comprising a eutectic composition selected from gold/silicon, gold/germanium, gold/tin, gold/indium, lead/tin, lead/indium, and platinum/silicon. The heating could comprise, for example, localized resistive heating using a patterned resistor, or could be provided by a laser.

In still other embodiments, the hermetic sealing material of the hermetic sealing substrate can comprise a metal gasket and a compressive force could be applied in an amount effective to deform the metal gasket around each reservoir opening. Tapered structures extending from the primary substrate surface could be used to concentrate the compressive forces at areas around the reservoir opening.

The hermetic sealing substrate preferably comprises or consists of a metal film or metal foil. In other embodiments, the hermetic sealing materials of the primary substrate, of the sealing substrate, or both, can comprise, for example, a silicate glass and/or a metal selected from gold, platinum, titanium, palladium, tantalum, aluminum, and stainless steel. Preferably, the primary substrate comprises a hermetic material selected from the group consisting of ceramics, metals, silicon, or glasses.

In some embodiments, the hermetic sealing substrate is a reservoir cap which can selectively be disintegrated to release or expose the molecules or secondary device. In a preferred embodiment, the molecules are drug molecules. In one method to form reservoir caps, the front side of the substrate comprises metal traces and the hermetic sealing substrate is welded onto the metal traces. In other embodiments of the sealing method, the reservoir end distal the opening in need of sealing comprises the reservoir caps.

In one embodiment, the method includes the optional step of applying a protective coating material, such as a polymer, over the hermetic sealing substrate, on a surface distal the surface that contacts the hermetic sealing materials of the primary substrate, before or after the reservoirs are hermetically sealed.

In another embodiment, the hermetic sealing substrate is a multi-layered structure comprising a glass layer which is anodically bonded to the primary substrate, wherein the glass layer has apertures in communication with the reservoirs. The multi-layered structure can further include a patterned metal layer which is anodically or eutectically bonded to the glass layer on the side distal the primary substrate, wherein the patterned metal layer has apertures in communication with the reservoirs and with the apertures in the glass layer. The multi-layered structure can further comprise a metal foil which is laser welded to the patterned metal layer on the side distal the glass layer, to hermetically seal the space defined by the reservoirs and apertures.

In one aspect, a method is provided for packaging an active-release microchip device which comprises: (1) providing a microchip device having a substrate, a plurality of reservoirs containing contents for release or exposure, and reservoir caps over the reservoir contents; (2) providing a hermetic packaging structure; and (3) forming a hermetic seal between the substrate of the microchip device and one or more surfaces of the packaging structure, effective to encase the microchip device yet leave the reservoir caps exposed and operational. The forming step can, for example, comprise laser welding, ultrasonic welding, or both. Alternatively, the forming step can include electroplating a metal across an interface between a surface of the substrate and a surface of the packaging structure. In another embodiment, the hermetic seal can include a eutectic bond. The packaging structure can further comprise power sources, control electronics, or a combination thereof, for powering disintegration of the reservoir caps, controlling the activation time of for disintegration of the reservoir caps, or both.

In one embodiment, the packaging structure comprises two metal pieces which are laser welded together after encasing the substrate between portions of the two pieces. In another embodiment, the packaging structure is a single piece.

DETAILED DESCRIPTION OF THE INVENTION

Figure 1:
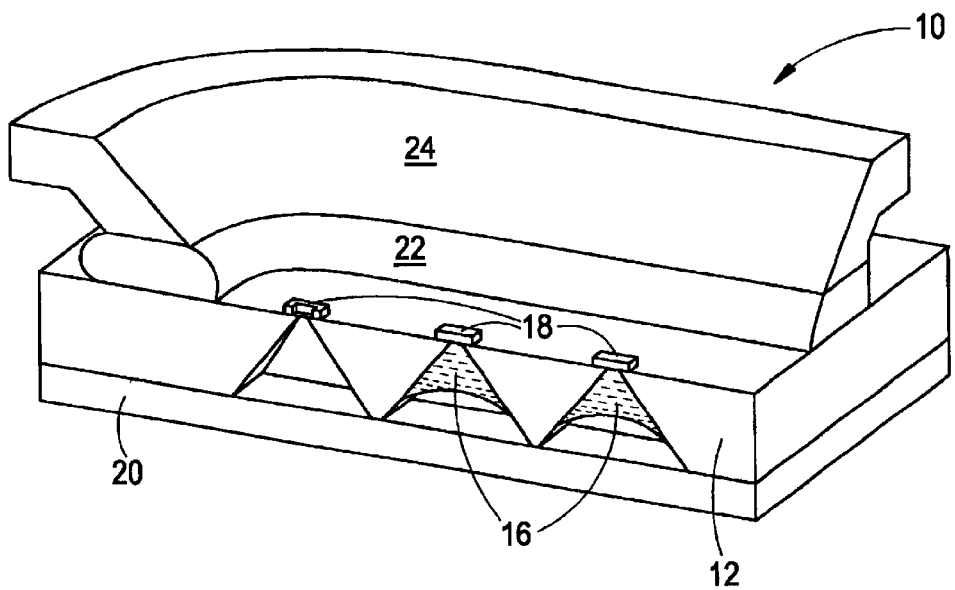
FIG. 1 is a cross-sectional and perspective view of one embodiment of hermetic seal locations that are incorporated within a microchip reservoir device.

Improved methods and devices have been developed to hermetically seal microchip reservoir devices. As used herein, the term "hermetic" refers to preventing undesirable ingress or egress of chemicals into or from one or more compartments of the device, particularly the device reservoirs, over the useful life of the device, using a seal is composed of materials, such as ceramics, glasses, and metals, which are essentially impermeable to chemicals and biological fluids, including such as water, air, and carbon dioxide. The seal is formed to prohibit permeation of chemicals through the sealing interface by positioning the opposing sealing materials' surfaces in intimate contact and applying thermal, mechanical, and/or chemical energy to produce a hermetic seal.

The microchip devices incorporating one or more of these hermetic seals include a substrate having a plurality of reservoirs that contain reservoir contents. The reservoirs can be individually filled and addressed, enabling the time and rate of release or exposure of multiple contents to be controlled. The reservoirs are closed at a first surface of the substrate by a reservoir cap. Controlled release or exposure of reservoir contents is via a reservoir opening through this first surface following opening of the reservoir cap. For those embodiments where the reservoir initially extends all the way through the substrate, the reservoirs also are closed at a second surface of the substrate distal the first surface. In either embodiment, the reservoir is sealed following filling of the reservoir with the reservoir contents, so that the reservoir contents are protected from the environment until exposure to the environment is desired. The microchip devices can further include a packaging structure hermetically bonded to a surface of the device substrate in order to protect the electronic systems (which control the release mechanisms) of the device from the environment, especially for implantation for use in in vivo applications. As used herein, the "environment" refers to the environment external the reservoirs, including, but not limited to, biological fluids and tissues at a site of implantation, air, fluids, and particulates present during storage or in vitro use of the microchip devices.

Device Components and Materials

The hermetically sealed microchip device includes a substrate having reservoirs, which are covered by reservoir caps and which contain reservoir contents (e.g., a drug, a sensor), and means for selectively opening the reservoir caps to release or expose the reservoir contents. The substrate, reservoirs, reservoir caps, reservoir contents, as well as control circuitry and power sources for actively controlling the cap opening, are described below and in U.S. Pat. Nos. 5,797,898 and 6,123,861, as well as PCT WO 02/30401, WO 02/30264, WO 01/91902, WO 01/64344, WO 01/41736, WO 01/35928, and WO 01/12157. The microchip devices further include one or more hermetic sealing elements, which hermetically seal the reservoirs, device electronics, or both.

Substrate

The substrate (also call the "primary substrate") contains the reservoirs and serves as the support for the microchip. Any material which can serve as a support, which is suitable for etching or machining or which can be cast or molded, and which is impermeable (during the time scale of the microchip's use) to the contents of the reservoir and to the surrounding environment may be used as a substrate. Suitable materials include metals, semiconductors, and ceramic materials. An example of a suitable semiconductor material includes silicon. Representative examples of ceramic materials include alumina (aluminum oxide), aluminum nitride, silicon dioxide, silicon nitride, and other various nitrides and oxides. The substrate can be formed of only one material or can be a composite or multi-laminate material.

For in vivo applications, the substrate generally is formed of or coated with a biocompatible material. Non-biocompatible materials may be encapsulated or contained in a biocompatible material, such as parylene, poly(ethylene glycol), polytetrafluoroethylene-like materials, or titanium, before use. For in vitro applications, such as in medical diagnostics, the substrate can be constructed of biocompatible or non-biocompatible materials.

Molecules and Secondary Devices (Reservoir Contents)

The reservoirs contain molecules, secondary devices, or combinations thereof, that need to be protected from surrounding environmental components until their release or exposure is desired. Proper functioning of certain reservoir contents, such as a catalyst or sensor, generally does not require their release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir.

Molecules

The reservoir contents can include essentially any natural or synthetic, organic or inorganic molecule or mixture thereof, for release (i.e. delivery) or retained and exposed. The molecules (i.e. chemicals) may be in pure solid, liquid, or gel form, or mixed with other materials that affect the release rate and/or time. Chemicals may be in the form of solid mixtures including, but not limited to, amorphous and crystalline mixed powders, monolithic solid mixtures, lyophilized powders, and solid interpenetrating networks; in the form of liquid mixtures including, but not limited to, solutions, emulsions, colloidal suspensions, and slurries; and in the form of gel mixtures including, but not limited to, hydrogels.

For in vivo applications, the chemical preferably is a therapeutic, prophylactic, or diagnostic agent. In one embodiment, the microchip device is used to deliver drugs systemically to a patient in need thereof. In another embodiment, the construction and placement of the microchip in a patient enables the local or regional release of drugs that may be too potent for systemic delivery of an effective dose. As used herein, "drugs" include any therapeutic, prophylactic or diagnostic agent, including organic or inorganic molecules, proteins, nucleic acids, polysaccharides and synthetic organic molecules, having a bioactive effect. Representative examples include analgesics, steroids, cytokines, psychotropic agents, chemotherapeutic agents, hormones, anesthetics, vaccines, metabolites, sugars, immunomodulators, antioxidants, ion channel regulators, and antibiotics. An example of a diagnostic agent is an imaging agent such as a contrast agent. The drugs can be in the form of a single drug or drug mixtures and can include pharmaceutically acceptable carriers.

For in vitro applications, the molecules can be any of a wide range of molecules where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures. In other embodiments, the molecules to be released are perfumes, fragrances, dyes, coloring agents, sweeteners, or a variety of other compounds, which for example, may be useful to release as a function of temperature change. In yet other embodiments, the reservoirs contain immobilized molecules. Examples include any chemical species which can be involved in a reaction, including, but not limited to, reagents; catalysts, including enzymes, metals, and zeolites; proteins; nucleic acids; polysaccharides; polymers; cells, as well as organic or inorganic molecules, including diagnostic agents.

The molecules can be provided as part of a release system. As used herein, "release system" includes the situation where the molecules are in pure form, as either a solid or liquid, or are in a matrix formed of biodegradable material or a material which releases incorporated molecules by diffusion or disintegration of the matrix. The degradation, dissolution, or diffusion properties of the release system can provide a method for controlling the release rate of the molecules. The molecules can be homogeneously or heterogeneously distributed within the release system. Selection of the release system is dependent on the desired rate of release of the molecules.

Both non-degradable and degradable release systems can be used for delivery of molecules. Suitable release systems include polymers, polymeric matrices, non-polymeric matrices, and inorganic and organic excipients and diluents. Examples of such excipients and diluents include calcium carbonate and sugar. Release systems may be natural or synthetic, although synthetic release systems are preferred due to the better characterization of release profiles. The release system is selected based on the period over which release is desired, generally in the range of at least one to twelve months for in vivo applications. In contrast, release times as short as a few seconds may be desirable for some in vitro applications. In some cases, continuous (constant) release from a reservoir may be most useful. In other cases, pulsed (variable) release from a reservoir may provide results that are more effective.

Pulsatile release can be achieved from an individual reservoir, from a plurality of reservoirs, or a combination thereof. For example, where each reservoir provides only a single pulse, multiple pulses (i.e. pulsatile release) are achieved by temporally staggering the single pulse release from each of several reservoirs. Alternatively, multiple pulses can be achieved from a single reservoir by incorporating several layers of a release system and other materials into a single reservoir.

Continuous release can be achieved by incorporating a release system that degrades, dissolves, or allows diffusion of molecules through it over an extended period. In addition, continuous release can be approximated by releasing several pulses of molecules in rapid succession ("digital" release, analogous to the digital storage and reproduction of music). Active and passive release systems can be combined. For example, a metal film or membrane reservoir cap, which is removed actively, can cover a passive release system that only begins its passive release after the metal film has been actively removed. Alternatively, a given substrate can include both passive and active release reservoirs.

The release system material can be selected so that molecules of various molecular weights are released from a reservoir by diffusion out or through the material or degradation of the material. Biodegradable polymers, bioerodible hydrogels, and protein delivery systems are preferred for release of molecules by diffusion, degradation, or dissolution. In general, these materials degrade or dissolve either by enzymatic hydrolysis or exposure to water in vivo or in vitro, or by surface or bulk erosion. Representative synthetic, biodegradable polymers include polyamides such as poly(amino acids) and polypeptides; polyesters such as poly(lactic acid), poly(glycolic acid), poly(lactic-co-glycolic acid), and polycaprolactone; polyanhydrides; polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include polyethers such as poly(ethylene oxide), poly(ethylene glycol), and poly(tetramethylene oxide); vinyl polymers—polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); polyurethanes; cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

The release system may include a pharmaceutical excipient. Suitable pharmaceutically acceptable excipients include most carriers approved for parenteral administration, including water, saline, Ringer's solution, Hank's solution, and solutions of glucose, lactose, dextrose, ethanol, glycerol, albumin, and the like. The release system may optionally include stabilizers, antioxidants, antimicrobials, preservatives, buffering agents, surfactants, and other additives useful for storing and releasing molecules from the reservoirs in vivo.

Secondary Devices

As used herein, unless explicitly indicated otherwise, the term "secondary device" includes, but is not limited to, any device and component thereof which can be located in or designed to operably communicate with one or more reservoirs in a microchip device. In a preferred embodiment, the secondary device is a sensor or sensing component. As used herein, a "sensing component" includes, but is not limited to, a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Secondary devices are further described in PCT WO 01/64344.

Examples of sensing components include components utilized in measuring or analyzing the presence, absence, or change in a drug, chemical, or ionic species, energy (or light), or one or more physical properties (e.g., pH, pressure) at a site. In a preferred embodiment, the microchip device is implantable in a patient (e.g., a human or other mammal) and includes sensors for monitoring the levels of glucose or urea in blood and other body fluids.

There are several different options for receiving and analyzing data obtained with devices located in the microchip devices. Typically, the operation of the microchip system will be controlled by an on-board (i.e. within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a microbattery or remotely by wireless transmission.

In one embodiment, the microchip device includes both drug and a sensor or sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The "sensing component" includes, but is not limited to, a component utilized in measuring or analyzing the presence, absence, or change in a chemical or ionic species, energy, or one or more physical properties (e.g., pH, pressure). Types of sensors include biosensors, chemical sensors, physical sensors, or optical sensors. Such sensors and sensor components are further described in PCT WO 01/64344. The sensor or sensing component detects (or not) the species or property at the site of in vivo implantation (e.g., in a bodily fluid or tissue), and further may relay a signal to the microprocessor used for controlling release from the microchip device, as detailed below. Such a signal could provide feedback on and/or finely control the release of parathyroid hormone. There are several different options for receiving and analyzing data obtained with devices located in the microchip devices. Active microchip devices may be controlled by local microprocessors or remote control. Biosensor information may provide input to the controller to determine the time and type of activation automatically, with human intervention, or a combination thereof.

In one embodiment, the microchip device includes one or more biosensors (which may be sealed in reservoirs until needed for use) that are capable of detecting and/or measuring signals within the body of a patient. As used herein, the term "biosensor" includes, but is not limited to, sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

Reservoir Caps

As used herein, the term "reservoir cap" includes a membrane or other structure suitable for separating the contents of a reservoir from the environment outside of the reservoir. It generally is self-supporting across the reservoir opening, although supports could be built into the cap. Selectively removing the reservoir cap or making it permeable will then "expose" the contents of the reservoir to the environment (or selected components thereof) surrounding the reservoir. In preferred embodiments, the barrier layer can be selectively disintegrated, e.g., on demand. As used herein, the terms "disintegrate," "disintegration," and "disintegrating" in reference to reservoir caps include any mechanism of loss of structural integrity and thus loss of barrier to the environment outside of the reservoir, including, but not limited to, oxidation, mechanical rupture, degradation or dissolving, unless otherwise indicated. The "mechanical rupture" typically does not include puncturing the reservoir cap from the outside, such as with a needle. In one embodiment, the reservoir cap is composed of a metal, such as copper, gold, and silver, which is disintegrated by electrochemical dissolution via the application of electrical potential, as described in U.S. Pat. No. 5,797,898 to Santini.

In active devices, the reservoir cap includes any material that can be disintegrated or permeabilized in response to an applied stimulus (e.g., electric field or current, magnetic field, change in pH, or by thermal, chemical, electrochemical, or mechanical means). In one embodiment, the reservoir cap is a thin metal membrane and is impermeable to the surrounding environment (e.g., body fluids or another chloride containing solution). Based on the type of metal and the surrounding environment, a particular electric potential is applied to the metal reservoir cap, which is then oxidized and disintegrated by an electrochemical reaction, to expose the contents of the reservoir to the surrounding environment. Examples of suitable reservoir cap materials include gold, silver, copper, and zinc. Any combination of passive or active barrier layers can be present in a single microchip device.

Means for Controlling Release or Exposure

Typically, the operation of the microchip system will be controlled by an on-board (i.e. within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a microbattery or remotely by wireless transmission.

Means for controllably releasing the molecules from active devices require actuation, which typically is done under the control of a microprocessor. For example, in one embodiment, the microchip device includes a substrate having a two-dimensional array of reservoirs arranged therein, a release system comprising drug molecules contained in the reservoirs, anode reservoir caps covering each of the reservoirs, cathodes positioned on the substrate near the anodes, and means for actively controlling disintegration of the reservoir caps. Preferably, such means includes an input source, a microprocessor, a timer, a demultiplexer, and a power source. The power source provides energy to drive the reaction between selected anodes and cathodes. Upon application of a small potential between the electrodes, electrons pass from the anode to the cathode through the external circuit causing the anode material to oxidize and dissolve into the surrounding fluids, exposing the release system containing the molecules for delivery to the surrounding fluids, e.g., in vivo. The microprocessor directs power to specific electrode pairs through a demultiplexer as directed, for example, by a PROM, remote control, or biosensor.

The microprocessor is programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor.

The control circuitry typically includes a microprocessor, a timer, a demultiplexer, and an input source (for example, a memory source, a signal receiver, or a biosensor), and a power source. The timer and demultiplexer circuitry can be designed and incorporated directly onto the surface of the microchip during electrode fabrication. The criteria for selection of a microprocessor are small size, low power requirement, and the ability to translate the output from memory sources, signal receivers, or biosensors into an address for the direction of power through the demultiplexer to a specific reservoir on the microchip device (see, e.g., Ji, et al., *IEEE J. Solid-State Circuits* 27:433–43 (1992)). Selection of a source of input to the microprocessor such as memory sources, signal receivers, or biosensors depends on the microchip device's particular application and whether device operation is preprogrammed, controlled by remote means, or controlled by feedback from its environment (i.e. biofeedback).

The criteria for selection of a power source are small size, sufficient power capacity, the ability to be integrated with the control circuitry, the ability to be recharged, and the length of time before recharging is necessary. Batteries can be separately manufactured (i.e. off-the-shelf) or can be integrated with the microchip itself. Several lithium-based, rechargeable microbatteries are described in Jones & Akridge, "Development and performance of a rechargeable thin-film solid-state microbattery", *J. Power Sources*, 54:63–67 (1995); and Bates et al., "New amorphous thin-film lithium electrolyte and rechargeable microbattery", *IEEE 35$^{th}$ International Power Sources Symposium*, pp. 337–39 (1992). These batteries are typically only ten microns thick and occupy 1 cm$^2$ of area. One or more of these batteries can be incorporated directly onto the microchip device. Binyamin, et al., *J. Electrochem. Soc.*, 147:2780–83 (2000) describes work directed toward development of biofuel cells, which if developed, may provide a low power source suitable for the operation of the present microchip devices and other microelectronic devices in vivo.

A microprocessor is used in conjunction with a source of memory such as programmable read only memory (PROM), a timer, a demultiplexer, and a power source such as a microbattery or a biofuel cell. A programmed sequence of events including the time a reservoir is to be opened and the location or address of the reservoir is stored into the PROM by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

The manufacture, size, and location of the power source, microprocessor, PROM, timer, demultiplexer, and other components are dependent upon the requirements of a particular application. In one embodiment, the memory, timer, microprocessor, and demultiplexer circuitry is integrated directly onto the surface of the microchip. The microbattery is attached to the other side of the microchip and is connected to the device circuitry by vias or thin wires. However, in some cases, it is possible to use separate, prefabricated, component chips for memory, timing, processing, and demultiplexing. In one embodiment, these components are attached to the back side of the microchip device with the battery. In another embodiment, the component chips and battery are placed on the front of or next to the microchip device, for example similar to how it is done in multi-chip modules (MCMs) and hybrid circuit packages. The size and type of prefabricated chips used depends on the overall dimensions of the microchip device and the number of reservoirs, and the complexity of the control required for the application.

Welding and Sealing Materials

A variety of metals, glasses, ceramics, and combinations thereof can be used to form the hermetic seals. The sealing material can be provided in the form of a thin foil that is welded or chemically bonded to one or more surfaces of the device, or alternatively, the sealing material can be provided in the form of a deposited film on another material or structure. For example, two substrates could be bonded together, with one surface of one substrate providing the sealing material for the other. In any event, effective bonding depends on the surface chemistry at the interface of the sealing material and the substrate. The sealing material is bonded to the substrate along the sealing surfaces on the back side of the substrate between the reservoirs, thereby isolating each reservoir.

In a preferred embodiment, particularly for ultrasonic welding, the sealing material is a metal foil, preferably having a thickness between about 1 and 50 $\mu$m. A defect-free gold foil is preferred, although other biocompatible, weldable metals are suitable. Examples of other suitable metals include platinum and titanium, as well as various alloys such as stainless steels and low melting temperature alloys.

The term "layer" as used herein in reference to metals generally refers to thin metal structures made by a deposition technique, such as e-beam or sputtering. The term "foil" as used herein generally refers to thicker metal structures made by rolling or shaping molten material. The term "layer" can however include foils, unless otherwise indicated.

In another similar embodiment, the sealing material is a reservoir cap material, which is welded to the front side of the substrate over the reservoir opening. In this embodiment, the reservoir cap preferably is a metal foil. The reservoir cap should be thick enough to be weldable, yet thin enough to be degradable.

The sealing material also may be or include silicon or glass. Glass, like metal, can provide a hermetic seal. In one embodiment, a hermetic seal is formed using a glass substrate having a metallic surface that will react, i.e. form a eutectic, with one or more surfaces of the substrate, e.g., the outer surfaces of the substrate between the reservoirs (i.e. the reservoir "streets") upon application of laser energy. Examples of the eutectic compositions include, but are not limited to Au/Si, Au/Ge, Au/Sn, Pb/Sn, Pb/In, Pt/Si, Ag/In, Al/Cu. (The lead and silver containing compositions typically would be used only for in vitro applications.)

The sealing can also be formed by directly using laser welding techniques to directly melt and bond two glass surfaces. One skilled in the art can select the proper glass chemistry and wavelength of light that will result in melting and mixing of these glass materials at the seal interface. Other laser welding examples rely on the formation of metallic bonds that can be formed using pure metallic species as well as various alloys. Representative examples of laser weldable metallics include titanium, stainless steels, platinum, palladium, and gold.

Other materials which could be suitable for welding include titanium, aluminum, gold/silicon, and nickel-titanium alloys (e.g., Ninitol, which exhibits super-elastic and shape-memory effects).

The sealing material optionally is provided, after welding, with an overcoat layer to increase the mechanical strength of the seal, to enhance the biocompatibility of the device, to serve as a secondary (i.e. back up) sealing mechanism, or to provided a combination of these functions. In one embodiment, the overcoat layer is a coating of biocompatible polymeric materials, such as poly(hydroxy acid) or poly(lactic acid), an epoxy, a polyurethane, a latex, a silicone, or a parylene.

Optionally, a layer of a barrier material, such as a wax or poly(ethylene oxide), can be included in the reservoir prior to placement and bonding of the sealing material to isolate or insulate the drug or other reservoir contents from the sealing energy.

Methods of Making and Sealing the Microchip Devices

The basic microchip devices (i.e. substrate, reservoirs, reservoir caps, release system, and control means) can be made using microfabrication methods known in the art, particularly those methods described in U.S. Pat. No. 5,797, 898; U.S. Pat. No. 6,123,861; PCT WO 01/41736, and WO 01/91902, which are hereby incorporated by reference in their entirety. These basic structures are then hermetically sealed as described herein.

There are several approaches available for forming the hermetic seal. One sealing technique is laser welding in which the weld materials maybe the same or dissimilar compositions, such as titanium (Ti), tantalum (Ta), palladium (Pd), platinum (Pt), stainless steel or silicate glasses. A second embodiment uses ultrasonic energy, and the sealing material preferably is a thin ductile metal foil, such as gold. A third embodiment uses resistive heating to initiate a reaction between the two mating surfaces. A specific example would be resistive heating of either a silicon (Si) or gold (Au) trace, which is in intimate contact with its counterpart yielding a eutectic Au/Si reaction. A eutectic reaction is useful because it occurs at a temperature that is lower than the melting temperatures of either of the component sealing materials.

As illustrated in FIG. 1, there generally are two hermetic seal locations incorporated within the microchip reservoir device. Microchip device 10 includes a substrate 12 having reservoirs 14, the right and center of which contain reservoir contents 16. The reservoirs 14 are closed off on the front side 11 of the substrate 12 by reservoir caps 18 (although the left reservoir cap is shown with an aperture, through which the reservoir contents of that reservoir were released). The two general seal locations are the back side reservoir seal 20 and the front side seal 22. The back side seal 20 represents the hermetic seal that chemically isolates individual reservoirs from each other and from their surrounding environment, by preventing ingress of environmental components (e.g., air, water) as well as preventing egress of the reservoir contents (e.g., drug molecules. The front side seal 22 represents the bond with device enclosure 24 that hermetically protects the contents of the packaging structure (not shown—including active control devices such as a battery, multiplexers, etc.) from the surrounding environment.

Hermetically Sealing the Reservoirs

Generally, the back side sealing method comprises (i) providing a microchip device substrate having a front side and a back side, wherein the back side has a plurality of reservoir openings in need of sealing; (ii) providing a back side substrate surface that is composed of one or more sealing materials, (iii) providing a thin substrate having at least one surface composed of one or more sealing materials, (iv) positioning the thin substrate over the reservoir openings, and (v) contacting the sealing surfaces together to seal the reservoir openings, wherein the contacting is effective to form a hermetic seal. This contacting step may or may not require chemical interaction or reaction (e.g., welding or bonding).

Figure 2:
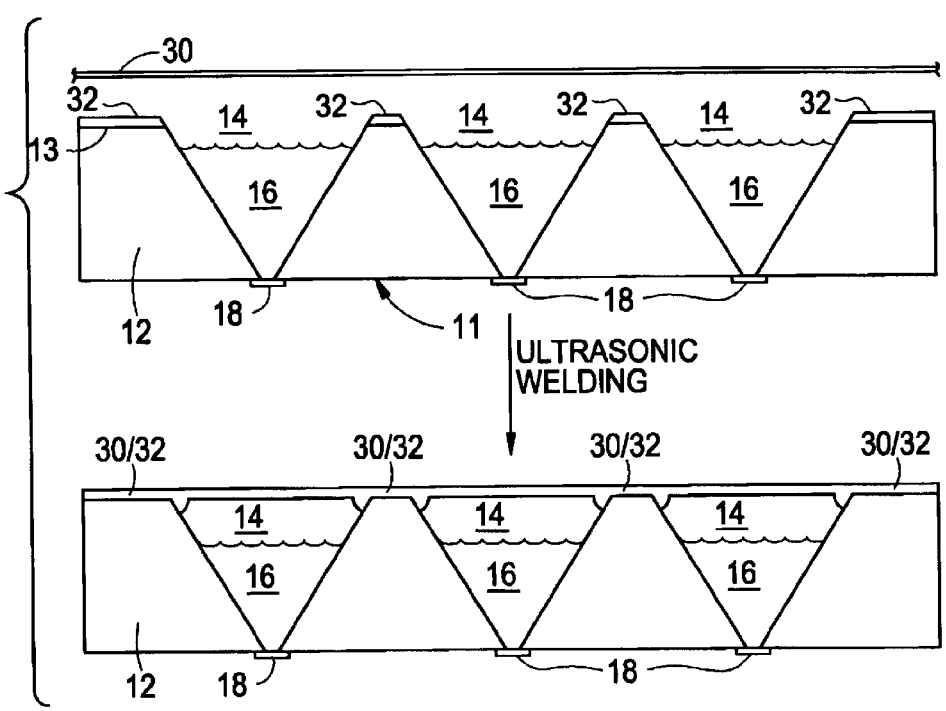
FIG. 2 illustrates a cross-sectional view of one embodiment of a microchip device before and after the open reservoirs of the device are sealed using an ultrasonic welding process.

In forming the hermetic seal of the back side, the reservoirs of the microchip substrate can be sealed using thermal, mechanical, and/or chemical bonding techniques. In various embodiments, a sealing material is welded to the substrate along the sealing surfaces (i.e., the back side of the substrate between the reservoirs), thereby isolating each reservoir. FIGS. 2, 3, and 4, described below, illustrate some of these embodiments.

FIG. 2 illustrates an ultrasonic welding process being used to seal reservoirs of a microchip device. Device substrate 12 has reservoirs 14, loaded with reservoir contents 16. The reservoirs 14 are closed off on the front side 11 of the substrate 12 by reservoir caps 18. The back side surface of the substrate 12 is coated with a thin metal layer 32, at least along the streets and edges. A metal foil 30 is positioned over the back side of the substrate 12 over the open reservoirs. Then, ultrasonic welding is used to weld the metal foil 30, with metal layer 32, to the substrate streets and edges, sealing each reservoir. The combined metal at the weld are shown as 30/32. In one embodiment, the thin metal layer 32 and the metal foil 30 are both gold.

In an optional embodiment, a polymer coating (not shown) could be applied onto the outer surface of the metal foil following the welding process. Such a coating could provide extra reservoir sealing and/or improved biocompatibility for the device.

Figure 3A:
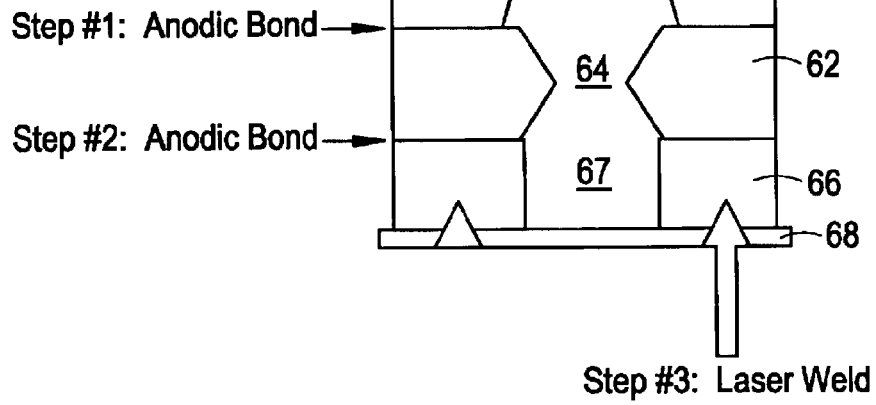
FIGS. 3A–C are cross-sectional views of various embodiments of a microchip device sealed using a Ti laser welding process.
Figure 3B:
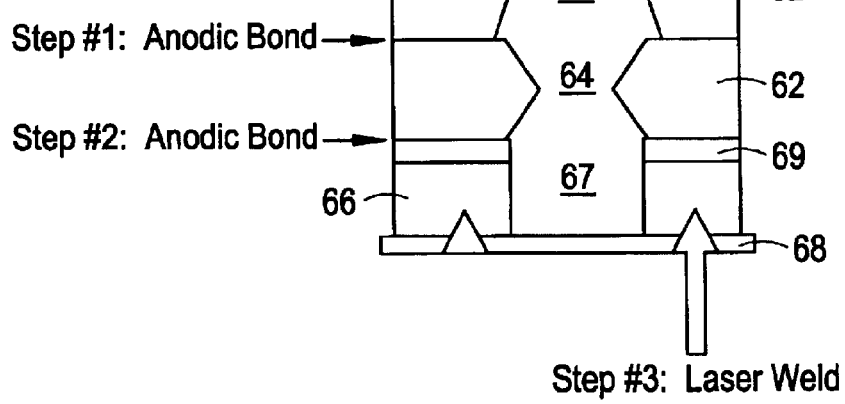
Figure 3C:
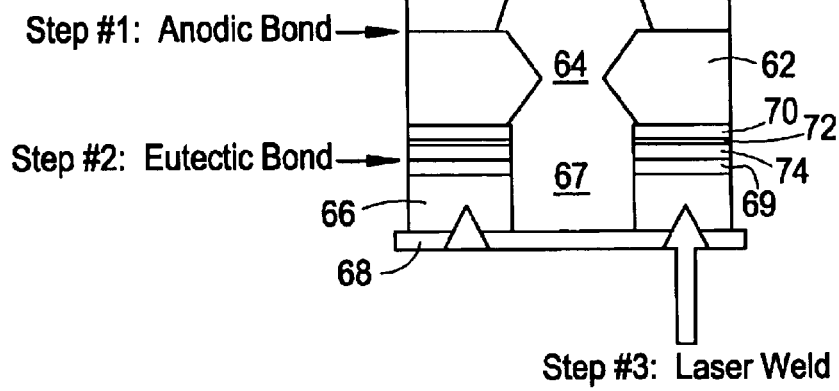
Figure 4:
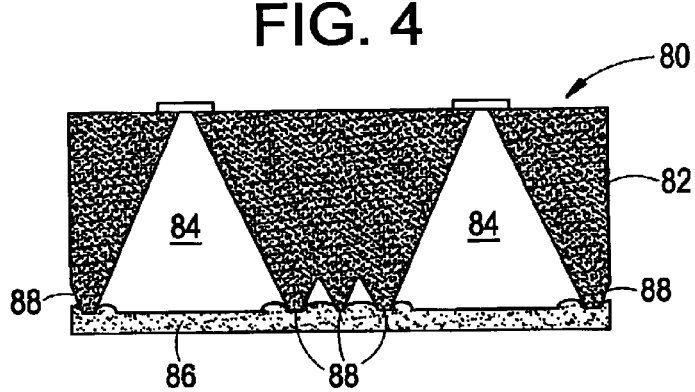
FIG. 4 is a cross-sectional view of one embodiment of a microchip device sealed with a metal gasket seal.

FIGS. 3A–C illustrate bonding and laser welding processes used to hermetically seal a reservoir substrate with a complex backing structure. In FIG. 3A, silicon substrate 52 has reservoir 54 closed off on front side 51 by reservoir cap 58. First, a glass layer 62 is anodically bonded to the backside of substrate 52, such that the aperture 64 in glass layer 62 is aligned with the opening of reservoir 54. Next, a patterned metal layer 66 is anodically bonded to the glass layer 62. The patterned (and etched) metal layer 66 also includes an aperture 67 that is aligned with aperture 64 and the opening of reservoir 54. Finally, a thin metal sheet 68 is laser welded to the patterned metal layer 66, sealing the space defined by reservoir 54, aperture 64, and aperture 67. In one embodiment, the glass layer 62 is 7740 glass (borosilicate) and the patterned metal layer 66 and thin metal sheet 68 are titanium. FIG. 3B illustrates a device made like that in FIG. 3A, except that patterned metal layer 66 further includes a thin (e.g., 2 micron) layer of silicon 69 which is anodically bonded to the glass layer 62. FIG. 3C illustrates a device made like that in FIG. 3B, except that a eutectic bond is used to attach the patterned metal layer 66 to the glass layer 62. To facilitate this, the glass layer 62 is provided with a 500 Angstrom layer of titanium 70, a 1000 Angstrom layer of platinum 72, and a 5 micron layer of gold 74. One skilled in the art can select other eutectic materials and thicknesses, and eutectic bonding techniques to form the eutectic bond (see Cheng, et al. "Localized Silicon Fusion and Eutectic Bonding for MEMS Fabrication and Packaging" J. MEMS vol. 9, no. 1 (March 2000) and Yao, et al. "Low Temperature Eutectic Bonding For In-Plane Type MicroThermoelectric Cooler" Proc. 2001 ASME Int'l Mech. Eng. Congress and Exposition, Nov. 11–16, 2001). The intermediate layers of the multilayer sealing structure described in FIGS. 3A–C advantageously serve to insulate the reservoir contents from heat generated in laser welding the outer metal foil, which is particularly advantageous when the reservoir contents includes temperature sensitive molecules or devices.

In another embodiment, hermetic sealing of the reservoirs is accomplished with the use of a metal gasket. The metal gasket is preferably a thin, ductile metal sheet, such as gold. One example is illustrated in FIG. 4, which shows device 80 having substrate 82 with reservoirs 84 sealed by gold metal gasket 86. In this embodiment, the metal gasket is a 50 micron gold sheet. The seal is created by applying a uniform compressive force that locally deforms the metal around the reservoir edges and streets. Plastic deformation occurs between individual reservoirs resulting in a hermetic interface. This deformation can be enhanced by providing the substrate with structural features to concentrate the compressive forces over small areas between adjacent reservoirs, as illustrated by tapered structures 88. Although not shown, the metal gasket typically would be packaged between a stiff (i.e. rigid) back plate and the back side of the substrate, so that the gasket is constrained between the stiff plate and the substrate. The gasket can be loaded in compression using mechanical fasteners or traditional welding techniques.

In preferred embodiments, the welding is achieved using acoustic, more preferably ultrasonic, energy. Ultrasonic welding is advantageous in that it requires no flux or shielding gas, and produces relatively little heat. Excessive heat could degrade a thermally labile chemical or drug in the reservoirs. Examples of ultrasonic welding methods are described in U.S. Pat. No. 5,651,494 to Ogino, et al. (welding different metals), and U.S. Pat. No. 5,785,786 to Suzuki et al (welding metal sheets). Other welding techniques that may be suitable include laser welding, e-beam welding, and RF welding, which are known in the art. Examples of laser welding and e-beam welding methods are described in U.S. Pat. No. 5,574,313 to McKleroy and in U.S. Pat. No. 4,093,843 to Lindstrom et al.

In the case of ultrasonic welding, all of the reservoirs can be sealed simultaneously by a planar welding tip the same size as the microchip substrate, or the reservoirs can be sealed one reservoir or one row at a time by an appropriately shaped ultrasonic horn, whether stationary or mobile. In a typical process, a welding horn is applied to the metal foil or other sheet of sealing material to bond it to the substrate surface, thereby sealing the reservoirs, and the opposing side of the substrate is in contact with the anvil of the acoustic welding machine.

In the case of laser welding and e-beam welding, the weld spot is formed by impinging the seal interface with an intense energy beam of either photons or electrons, effective to cause localized heating to fuse together the two adjacent surfaces. The weld "spot" typically has a diameter between about 10 and 300 μm. The energy beam can be guided along the seal interface such that the welds overlap, ultimately forming a hermetic bond.

Figure 5:
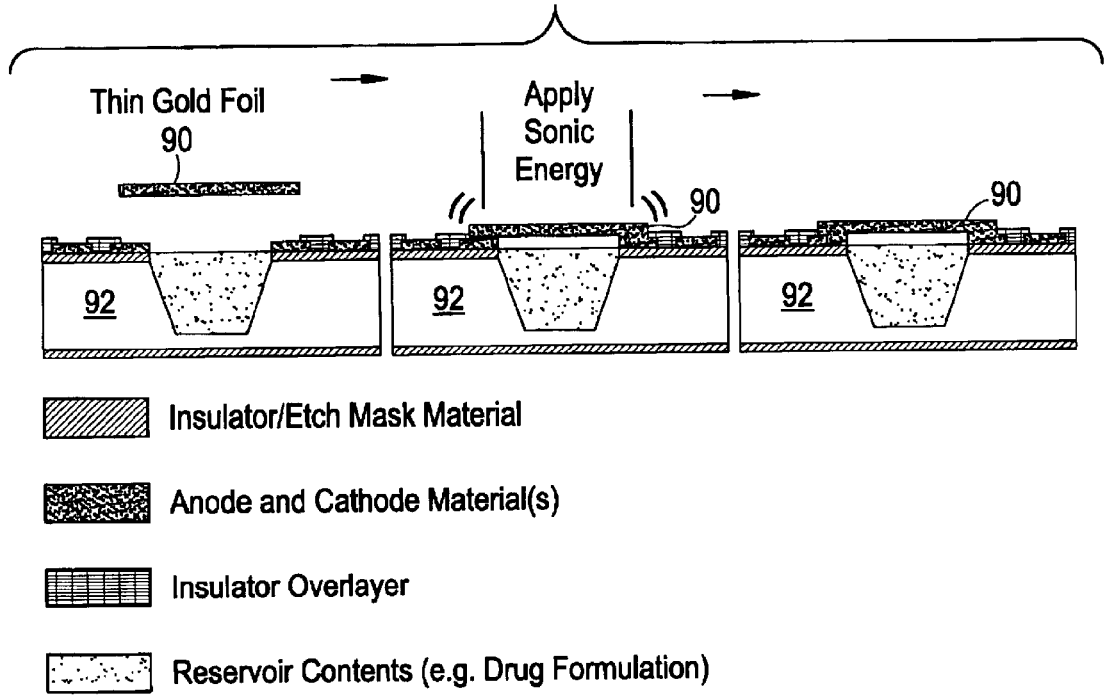
FIG. 5 is a cross-sectional view of one embodiment of a microchip device undergoing an ultrasonic welding process to bond a reservoir cap over a reservoir of the microchip device.

In another embodiment, the step of sealing and the step of formation of a reservoir cap over the reservoir opening can be combined. This is particularly useful for devices in which the reservoirs are filed and released from the same side, for example, in embodiments where the reservoirs are formed in a substrate without penetrating through the entire thickness of the substrate. One example of such a process is shown in FIG. 5, wherein a metal foil 90 is placed over reservoir contents in the reservoir in substrate 92 and then acoustic energy is applied to weld the foil, sealing the reservoir and forming metal reservoir cap 90. The welding preferably is achieved using ultrasonic energy. The reservoir cap preferably is a thin metal foil, such as gold.

Thus, in one embodiment, the microchip device fabrication process includes (i) providing a substrate having a front side and a back side, wherein the front side comprises a plurality of reservoirs; (ii) filling the reservoirs with reservoir contents for release or exposure; and (iii) capping the reservoir openings with a cap material which can be selectively disintegrated to release or expose the reservoir contents, wherein the capping step comprises welding the cap material to the front side of the substrate. The capping step preferably comprises positioning a metal foil (cap material) over the reservoir opening and then ultrasonically welding the cap material onto a metal trace deposited onto the front side of the substrate circumferential to the reservoir opening. In this embodiment, the reservoirs preferably are fabricated into the substrate such that an aperture is not formed; rather, the reservoir has a single opening through which both filling and release occur.

Packaging the Substrate Assembly

The hermetic sealing methods described above can be used in other aspects of the fabrication and assembly of the microchip devices. In particular, an active-release microchip device can be welded to one or more surfaces of a packaging structure. The term "packaging structure" refers to an enclosure, casing, or other containment device for encasing the microchip device, control electronics, and power elements (e.g., microbattery or devices for receiving wireless transmission of power), so as to expose only the front side of the substrate or reservoir caps. The term "microchip device" refers to either packaged or unpackaged devices, unless one or the other is expressly referenced.

Figure 6:
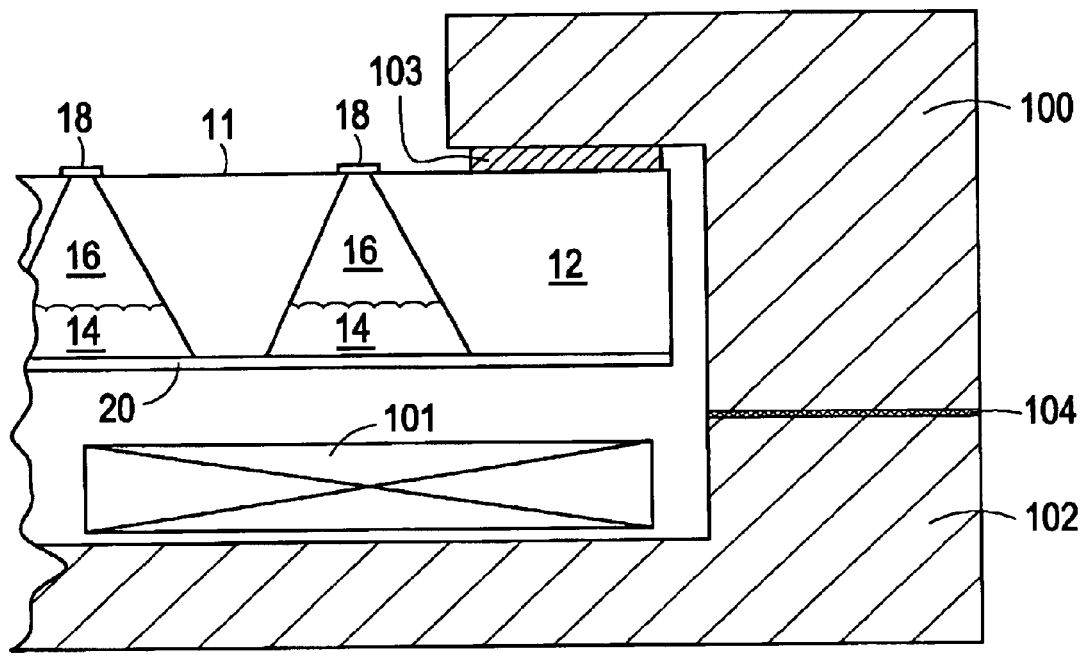
FIG. 6 is a cross-sectional view of one embodiment of a microchip substrate ultrasonically welded to a packaging structure for the microchip device.
Figure 7:
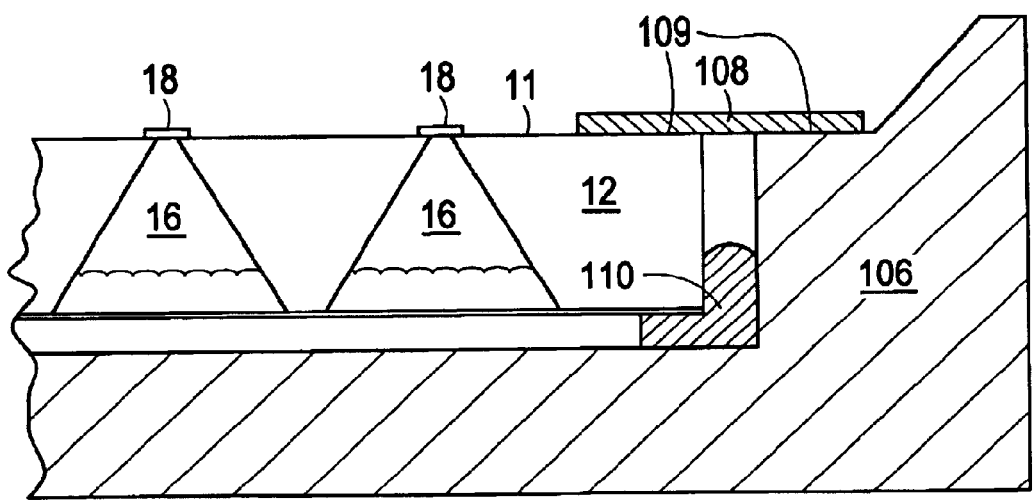
FIG. 7 is a cross-sectional view of another embodiment of a microchip substrate ultrasonically welded to a packaging structure for the microchip device.

In one embodiment, ultrasonic welding techniques are used to hermetically secure a device substrate to a packaging structure for the microchip device. Steps for such a "packaging" type of sealing method can include contacting a metal surface of the substrate with a metal surface of a packaging substrate and then applying ultrasonic energy to the interface so that deformation occurs at the metallic interface to produce a hermetic bond. Two variations of this approach are illustrated in FIGS. 6 and 7. In FIG. 6, the front surface 11 of substrate 12 is ultrasonically welded to a first piece 100 of a two-piece metal casing and then the first piece 100 can be laser welded to a second piece 102 of the two-piece metal casing. The hermetic bond 103 is formed where two gold layers (the outer surfaces thereof) have been contacted and ultrasonically welded, and the hermetic bond 104 is formed where the two casing pieces have been contacted and laser welded. Reference character 101 represents generic microchip device electronics, which are also encased by metal casing 100/102. In FIG. 7, a single one casing 106 is used, and a gold foil 108 positioned to bridge the front surface 11 of substrate 12 and a surface of the single piece casing 106. The foil 108 is then ultrasonically welded at points 109 to form a hermetic bond. In either embodiment, the packaging structure preferably is composed of a biocompatible metal, such as titanium, stainless steel, or an alloy thereof.

In a preferred embodiment for the formation of a front side hermetic microchip-to-package seal, the method comprises the steps of (i) providing a microchip device substrate having a front side and a back side, wherein the front side has surface composed of at least one sealing material; (ii) providing a packaging structure surface that is composed of a second at least one sealing material; (iii) aligning the front side of the substrate and the packaging structure surface so that the sealing surfaces mate; and (iv) bringing the first and second sealing materials into intimate contact effective to form a hermetic seal between the front side surface of the microchip and the packaging structure without obstructing the operation of the device.

Figure 8:
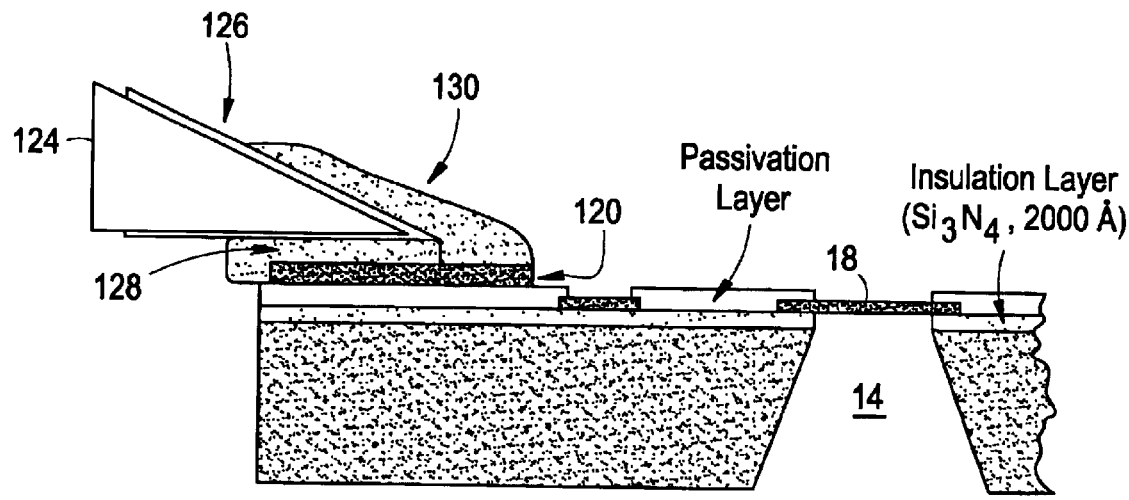
FIG. 8 is a cross-sectional view of one embodiment of a microchip substrate hermetically bonded to a packaging structure by electro-plating a gold film.

In an alternative approach, electroplating is used to form the hermetic bond between the front side surface of the microchip reservoir device and the packaging structure. An example of electroforming hermetic glass to metal seals is described in U.S. Pat. No. 3,932,227 to Rothenberg. In one embodiment of a front side electroformed hermetic seal, the method of fabrication comprises (i) metallizing and bringing into electrical contact the two mating surfaces, i.e. the front side surface of the microchip and a surface of the package; (ii) immersing this electrically conductive interface into an electroplating solution; (iii) and applying an electrical potential to the interface so that a metal layer is electro-deposited forming a hermetic "bridge" across the interface. Gold is a preferred plating material, as it provides a biocompatible surface. Such a technique could be performed prior to filling the reservoirs or subsequent to filling and sealing the reservoirs. A representative example is illustrated in FIG. 8. In this illustrated embodiment, a gold metallization ring 120 is deposited around the periphery of the collective the reservoir caps 18 (i.e. around the outer edge of the substrate) on the front side of the microchip device. The mating surface 122 of the titanium packaging structure 124 is metallized by depositing a thin gold layer 126. Next, these two surfaces (126 and 120) are secured together with, and in electrical contact through, a conductive epoxy 128, thus forming a seal interface consisting of layer 126, epoxy 128, and gold ring 120. This seal interface is then submerged in a electroplating solution, and an electro-plating potential is applied to form a hermetic bridge 130 across the seal interface.

Figure 9:
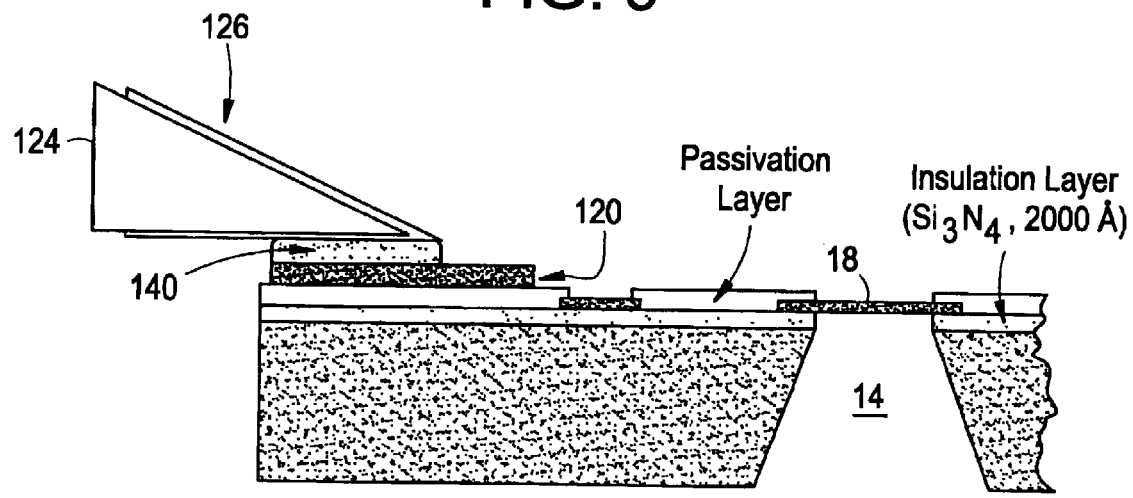
FIG. 9 is a cross-sectional view of one embodiment of a microchip substrate eutectically bonded to a packaging structure for the microchip device electronics.

Another example of a front side sealing technique is based on eutectic bonding. In one embodiment, a hermetic eutectic seal is formed by (i) depositing thin layers of materials in eutectic proportions onto the surfaces to be bonded; (ii) contacting these two mating surfaces, e.g., the front side surface of the microchip and the surface of the enclosure, together; and (iii) heating the interface to a temperature at which the two surfaces undergo the specified eutectic reaction. A specific surface configuration would be surface chemistries capable of forming the Au/Si eutectic composition, typically at a localized temperature of 363° C. A specific surface configuration would be surface chemistries capable of forming the Au/Si eutectic composition. Various applications of eutectic bonding to form hermetic seals are described in U.S. Pat. No. 6,148,673 to Brown (pressure sensor applications) and in U.S. Pat. No. 5,568,585 to Kramer (optical fiber applications). A representative example is illustrated in FIG. 9. In this illustrated embodiment, a gold metallization ring 120 is deposited around the periphery of the collective reservoir caps 18 on the front side of the microchip device. The mating surface 122 of the titanium packaging structure 124 is metallized by depositing a thin gold layer 126. Next, a gold/silicon eutectic composition 140 is formed at the interface of these two surfaces (126 and 120) to form a seal.

Surface Preparation

Sealing surfaces may be prepared to promote an effective seal. Such surfaces include the front side and the back side of the microchip substrate, as well as the side of the sealing material facing the substrate. For example, the silicon of the sealing surface of the substrate may be provided with an attached (mating) material, that is, a layer of material(s) to which the sealing material will bond. For instance, welding of a metal foil may be enhanced by depositing a metal, preferably the same composition as the metal foil, onto the substrate. The deposited mating material is intended to improve the quality of the bond by providing additional bonding sites. The mating material may be attached to the substrate by a variety of techniques. For example, it may be applied using MEMS techniques known in the art, for example, by using a combination of metal deposition and photolithography steps. The material may be deposited, for example, by electronic beam evaporation, sputtering, or plating.

In addition, one or both surfaces (i.e. sealing material and substrate) may be roughened or adhesion features may be micromachined into the surface of the substrate to enhance bonding.

For embodiments in which the reservoirs are filled prior to forming the seal, an insulating material, e.g., boro-silicate glass, is optionally patterned onto the surface of the microchip reservoir substrate between the outer most sealing surface and the sealing material (see FIGS. 3A–C). Such an insulating material may be used to minimize or eliminate electrical crosstalk (e.g., electrical shorts between the metallization layers within the seal and other electrodes on the device) and to limit the exposure of the reservoirs contents to sealing energy during the final bonding processing steps.

It may be desirable to apply a protective polymer coating (such as photoresist) on the front side of the substrate (e.g., over the reservoir caps) that is not removed until after filling and sealing are complete. This protective coating will support the reservoir caps to withstand the additional mechanical forces that may be introduced during the proceeding filling and sealing processes, such as by ultrasonic welding.

Post-Sealing Processes

The sealed microchip substrates may be further treated to improve the robustness and integrity of the seal. The devices may be inspected by a technique to determine whether the reservoirs have been completely sealed. An overcoat layer can be applied over the sealed substrate, for example with a vapor deposition technique, such as commonly used to apply a parylene coating on electronic devices. Sealing may be further enhanced with a mechanical sealing technique, for example by positioning and compressing the sealed substrate between a gasket material and sealing frame.

Following completion of the sealing process, any protective polymer coating can be removed with a solvent and/or oxygen plasma cleaning step, as known in the art.

Using the Microchip Devices

The hermetically sealed microchip devices described herein can be used in a wide variety of applications. Preferred applications include the controlled delivery of a drug, biosensing, or a combination thereof. For example, the hermetically sealed microchip devices are suitable for implantation into a patient, such as a human or other vertebrate animal, for controlled drug delivery, locally, regionally, or systemically. The microchip device can be implanted in vivo using standard surgical or minimally-invasive implantation techniques, e.g., via a catheter. The microchip devices are especially useful for drug therapies in which one needs to very precisely control the exact amount, rate, and/or time of delivery of the drug. Preferred drug delivery applications include the delivery of potent compounds, including both small and large molecules, such as hormones, steroids, chemotherapy medications, vaccines, gene delivery vectors, and some strong analgesic agents.

The passive or active devices have numerous in vivo, in vitro, and commercial diagnostic applications. The microchips are capable of delivering precisely metered quantities of molecules and thus are useful for in vitro applications, such as analytical chemistry and medical diagnostics, as well as biological applications such as the delivery of factors to cell cultures. In other applications, the devices are used to control release of fragrances, dyes, or other useful chemicals. Other methods of using the microchip devices for controlled release of drug and other molecules, as well as for controlled exposure and release of molecules or secondary devices, are described in U.S. Pat. Nos. 5,797,898 and 6,123,861; and PCT WO 02/30401, WO 02/30264, WO 01/91902, WO 01/64344, WO 01/41736, WO 01/35928, and WO 01/12157.

Modifications and variations of the methods and devices described herein will be obvious to those skilled in the art from the foregoing detailed description. Such modifications and variations are intended to come within the scope of the appended claims.

We claim:

1. A method for hermetically sealing reservoirs of a microchip device, the method comprising:

providing a primary substrate having a front side and a back side, the substrate comprising a plurality of reservoirs positioned between the front side and the back side, each reservoir being loaded with molecules or a secondary device for controlled release or exposure, the reservoirs having at least one opening in need of sealing, the primary substrate including one or more hermetic sealing materials;

providing a hermetic sealing substrate having a surface composed of one or more hermetic sealing materials;

positioning the hermetic sealing substrate over the reservoir openings and contacting said hermetic sealing materials of the primary substrate with said hermetic sealing materials of the hermetic sealing substrate; and applying energy to the contacted sealing materials effective to form a hermetic seal between the hermetic sealing substrate and the primary substrate to hermetically seal each of the reservoir openings.

2. The method of claim 1, wherein the energy is applied through a welding process.

3. The method of claim 2, wherein the welding process comprises ultrasonic welding.

4. The method of claim 2, wherein the welding process comprising laser welding.

5. The method of claim 1, wherein the energy is applied by heating to cause a reaction between the hermetic sealing materials of the primary substrate and the hermetic sealing materials of the hermetic sealing substrate.

6. A method for hermetically sealing reservoirs of a device, the method comprising:

providing a primary substrate having a front side and a back side, the substrate comprising a plurality of reservoirs positioned between the front side and the back side, each reservoir being loaded with molecules or a secondary device for controlled release or exposure, the reservoirs having at least one opening in need of sealing, the primary substrate including one or more hermetic sealing materials;

providing a hermetic sealing substrate having a surface composed of one or more hermetic sealing materials;

positioning the hermetic sealing substrate over the reservoir openings and contacting said hermetic sealing materials of the primary substrate with said hermetic sealing materials of the hermetic sealing substrate; and applying energy to the contacted sealing materials effective to form a hermetic seal between the hermetic sealing substrate and the primary substrate to hermetically seal the reservoir openings, wherein the energy is applied by heating to cause a eutectic reaction between the hermetic sealing materials of the primary substrate and the hermetic sealing materials of the hermetic sealing substrate.

7. The method of claim 6, wherein the eutectic reaction forms a eutectic bond comprising a eutectic composition selected from the group consisting of gold/silicon, gold/germanium, gold/tin, gold/indium, lead/tin, lead/indium, and platinum/silicon.

8. A method for hermetically sealing reservoirs of a device, the method comprising:

providing a primary substrate having a front side and a back side, the substrate comprising a plurality of reservoirs positioned between the front side and the back side, each reservoir being loaded with molecules or a secondary device for controlled release or exposure, the reservoirs having at least one opening in need of sealing, the primary substrate including one or more hermetic sealing materials;

providing a hermetic sealing substrate having a surface composed of one or more hermetic sealing materials;

positioning the hermetic sealing substrate over the reservoir openings and contacting said hermetic sealing materials of the primary substrate with said hermetic sealing materials of the hermetic sealing substrate; and applying energy to the contacted sealing materials effective to form a hermetic seal between the hermetic sealing substrate and the primary substrate to hermetically seal the reservoir openings, wherein the energy is applied by heating, which comprises resistive heating, to cause a reaction between the hermetic sealing materials of the primary substrate and the hermetic sealing materials of the hermetic sealing substrate.

9. A method for hermetically sealing reservoirs of a device, the method comprising:

providing a primary substrate having a front side and an back side, the substrate comprising a plurality of reservoirs positioned between the front side and the back side, each reservoir being loaded with molecules or a secondary device for controlled release or exposure, the reservoirs having at least one opening in need of sealing, the primary substrate including one or more hermetic sealing materials;

providing a hermetic sealing substrate having a surface composed of one or more hermetic sealing materials;

positioning the hermetic sealing substrate over the reservoir openings and contacting said hermetic sealing materials of the primary substrate with said hermetic sealing materials of the hermetic sealing substrate; and applying a mechanical force to the contacted sealing materials effective to form a hermetic seal between the hermetic sealing substrate and the primary substrate to hermetically seal the reservoir openings, wherein the hermetic sealing material of the hermetic sealing substrate comprises a metal gasket and the applied mechanical force is effective to deform the metal gasket so as to seal each reservoir opening.

10. The method of claim 9, further comprising tapered structures extending from the primary substrate surface and effective to concentrate the compressive forces at areas around the reservoir opening.

11. The method of claim 1, wherein the hermetic sealing substrate comprises a metal film or metal foil.

12. The method of claim 1, wherein the hermetic sealing materials of the primary substrate, of the sealing substrate, or both, comprise a silicate glass or silicon.

13. The method of claim 1, wherein the hermetic sealing materials of the primary substrate, of the sealing substrate, or both, comprise a metal selected from the group consisting of gold, platinum, titanium, palladium, tantalum, aluminum, and stainless steel.

14. The method of claim 1, wherein the primary substrate comprises a hermetic material selected from the group consisting of ceramics, metals, silicon, or glasses.

15. The method of claim 1, wherein, following formation of the hermetic seal, the hermetic sealing substrate is a reservoir cap which can selectively be disintegrated to release or expose the molecules or secondary device.

16. The method of claim 15, wherein the front side of the substrate comprises metal traces and the hermetic sealing substrate is welded onto the metal traces.

17. The method of claim 1, wherein the reservoir is closed, at the end distal the opening in need of sealing, by a reservoir cap which can selectively be disintegrated to release or expose the molecules or secondary device.

18. The method of claim 1, wherein the reservoirs contain drug molecules.

19. The method of claim 1, further comprising applying a protective coating material over the hermetic sealing substrate, on a surface distal the surface that contacts the hermetic sealing materials of the primary substrate, before or after the reservoirs are hermetically sealed.

20. A method of packaging a microchip device, comprising:

providing a microchip device having a substrate, a plurality of reservoirs containing contents for release or exposure, and reservoir caps over the reservoir contents, wherein each reservoir is hermetically sealed;

providing a hermetic packaging structure; and forming a hermetic seal between the substrate of the microchip device and one or more surfaces of the packaging structure, effective to encase the microchip device yet leave the reservoir caps exposed and operational.

21. The method of claim 20, wherein the forming step comprises laser welding, ultrasonic welding, or both.

22. A method of packaging a microchip device, comprising:

providing a microchip device having a substrate, a plurality of reservoirs containing contents for release or exposure, and reservoir caps over the reservoir contents;

providing a hermetic packaging structure; and forming a hermetic seal between the substrate of the microchip device and one or more surfaces of the packaging structure, effective to encase the microchip device yet leave the reservoir caps exposed and operational, wherein the forming step comprises electroplating a metal across an interface between a surface of the substrate and a surface of the packaging structure.

23. A method of packaging a microchip device, comprising:

providing a microchip device having a substrate, a plurality of reservoirs containing contents for release or exposure, and reservoir caps over the reservoir contents;

providing a hermetic packaging structure; and forming a hermetic seal between the substrate of the microchip device and one or more surfaces of the packaging structure, effective to encase the microchip device yet leave the reservoir caps exposed and operational, wherein the hermetic seal comprises a eutectic bond.

24. The method of claim 20, wherein the packaging structure comprises two metal pieces which are laser welded together after encasing the substrate between portions of the two pieces.

25. The method of claim 20, wherein the packaging structure further comprises power sources, control electronics, or a combination thereof, for powering disintegration of the reservoir caps, controlling the activation time of for disintegration of the reservoir caps, or both.

26. The method of claim 1, wherein the reservoirs each comprise a sensor or sensing component.

27. The method of claim 1, wherein the hermetic sealing materials of the primary substrate, of the sealing substrate, or both, comprise a metal or an alloy.

28. The method of claim 6, wherein the eutectic reaction forms a eutectic bond which includes a eutectic composition comprising indium or tin.

29. The method of claim 6, wherein the reservoirs each comprise a therapeutic or prophylactic agent.

30. The method of claim 6, wherein the reservoirs each comprise a sensor or sensing component.

31. The method of claim 9, wherein the reservoirs each comprise a therapeutic or prophylactic agent.

32. The method of claim 9, wherein the reservoirs each comprise a sensor or sensing component.

33. The method of claim 20, wherein the reservoirs contents comprise a therapeutic or prophylactic agent.

34. The method of claim 20, wherein the reservoirs contents comprise a sensor or sensing component.

35. The method of claim 28, wherein the eutectic bond includes a eutectic composition comprising indium or tin.

36. The method of claim 1, wherein the energy is applied to cause non-reactive fusion of the hermetic sealing material of the primary substrate with the hermetic sealing material of the hermetic sealing substrate.

37. The method of claim 8, wherein the resistive heating comprises use of a patterned resistor.

38. A method for hermetically sealing reservoirs of a device, the method comprising:

providing a primary substrate having a front side and a back side, the primary substrate comprising a plurality of reservoirs positioned between the front side and the back side, the reservoirs having at least one opening in need of sealing, the primary substrate including one or more hermetic sealing materials;

contacting the one or more hermetic sealing materials of the primary substrate to a glass layer of a multi-layer, secondary substrate, the glass layer having a plurality of apertures therethrough; and anodically bonding the glass layer to the one or more hermetic sealing materials of the primary substrate to form a hermetic seal between the primary substrate and the secondary substrate to hermetically seal the reservoir openings, wherein the apertures are in communication with the reservoirs.

39. The method of claim 38, wherein multi-layer, secondary substrate further comprises a patterned metal layer which is anodically or eutectically bonded to the glass layer on the side distal the primary substrate, the patterned metal layer having apertures in communication with the reservoirs and with the apertures in the glass layer.

40. The method of claim 39, wherein the multi-layer, secondary substrate further comprises a metal foil which is laser welded to the patterned metal layer on the side distal the glass layer, the metal sheet sealing the space defined by the reservoirs and apertures.

41. The method of claim 38, further comprising loading the reservoirs with reservoir contents for controlled release or exposure.

* * * * *